(12) United States Patent
Lin et al.

(10) Patent No.: US 7,826,056 B2
(45) Date of Patent: Nov. 2, 2010

(54) TESTING METHOD FOR TESTING COLOR WHEELS

(75) Inventors: Hsin-Li Lin, Taipei Hsien (TW); I-Pen Chien, Taipei Hsien (TW); Kuang-Wei Lin, Taipei Hsien (TW); Po-Yuan Lai, Taipei Hsien (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 408 days.

(21) Appl. No.: 12/108,054

(22) Filed: Apr. 23, 2008

(65) Prior Publication Data
US 2009/0033939 A1 Feb. 5, 2009

(30) Foreign Application Priority Data
Aug. 1, 2007 (CN) .................. 2007 1 0201229

(51) Int. Cl.
*G01N 21/25* (2006.01)
(52) U.S. Cl. ..................... 356/418; 356/4.01
(58) Field of Classification Search ............. 356/418, 356/4.01, 4.07, 152.1–152.3, 3, 140–141.3; 359/891
See application file for complete search history.

(56) References Cited

U.S. PATENT DOCUMENTS
7,314,282 B2 * 1/2008 Bhowmik ............... 353/84

FOREIGN PATENT DOCUMENTS
CN 101358841 A 2/2009

* cited by examiner

*Primary Examiner*—Gregory J Toatley
*Assistant Examiner*—Tri T Ton
(74) *Attorney, Agent, or Firm*—Andrew C. Cheng

(57) ABSTRACT

A testing method is configured for testing parameters of a color wheel. The color wheel includes a color filter, which includes three sector-shaped filter segments and a motor for driving the filter segments of the color filter to rotate. The color filter is driven to rotate. Light is emitted toward the color filter of the color wheel, and reflected back by the color filter. Boundary impulses are generated according to changes in intensity of the light reflected back by the color filter. Based on relationships between the boundary impulses, central angles of the filter segments of the color wheel are calculated.

13 Claims, 8 Drawing Sheets

TESTING METHOD FOR TESTING COLOR WHEELS

This application is related to co-pending U.S. patent application 12/108,039 entitled "TESTING SYSTEM FOR TESTING COLOR WHEELS" and filed on the same day as the instant application. The co-pending U.S. patent application is assigned to the same assignee as the instant application. The disclosure of the above-identified application is incorporated herein by reference.

BACKGROUND

1. Technical Field

The present invention generally relates to a method for testing color wheels, and particularly to a method for precisely measuring central angles of filter segments within a color wheel, along with an angular position of a timing mark on the color wheel.

2. Description of Related Art

Referring to FIGS. 7 and 8, a color wheel 10 of a projector system according to a related art is shown. The color wheel 10 includes a round color filter 100, a mounting portion 200, a motor 300 and a timing mark 400 adhered to a sidewall of the mounting portion 200. The color filter 100 is composed of three colored sector-shaped filter segments: a red filter segment 102, a green filter segment 104, and a blue filter segment 106. Because people perceive different colors at different response speeds, central angles of the red, green and blue filter segments 102, 104, 106 are designed to be different from each other. The timing mark 400 is arranged on the sidewall of the mounting portion 200.

While operating the projector system, the color filter 100 and the timing mark 400 are driven by the motor 300 to rotate together. The central angles of the filter segments 102, 104, 106 and the angular position of the timing mark 400 relative to the filter segments 102, 104, 106 can be detected to help the projector system recognize positions of the filter segments 102, 104, 106. In other words, the central angles of the filter segments 102, 104, 106 and the timing mark 400 help the projector system know which color is being displayed by the projector system at any given time. Therefore, the central angles of the filter segments 102, 104, 106 and the angular positions of the timing mark 400 are important parameters that influence the image quality produced by the projector system. If the central angles of the filter segments 102, 104, 106 and the actual angular position of the timing mark 400 relative to the filter segments 102, 104, 106 deviate significantly from the predetermined central angles of the filter segments 102, 104, 106 and predetermined angular position of the timing mark 400, the image quality of the projector system will be greatly degraded.

SUMMARY

The present invention provides a testing method for precisely measuring central angles of filter segments of a color wheel. The color wheel includes a color filter, which comprises three sector-shaped filter segments and a motor for rotating the filter segments. The testing method includes rotating the color filter, emitting light toward the color filter of the color wheel, receiving light reflected back by the color filter, generating a plurality of boundary impulses based on the changes in intensity of the reflected light, and calculating central angles of the filter segments within the color wheel based on relationships between the boundary impulses.

Other advantages and novel features of the present testing method will become more apparent from the following detailed description of preferred embodiments when taken in conjunction with the accompanying drawings.

DETAILED DESCRIPTION OF THE EMBODIMENTS

References will now be made to the diagrams to describe the various present embodiments in detail.

Currently, there are many kinds of color filters, such as RGB color filters, RGB and white color filters, and RGBRGB color filters. Hereinafter, an RGB color wheel is taken as an example to describe the testing system.

Figure 1:
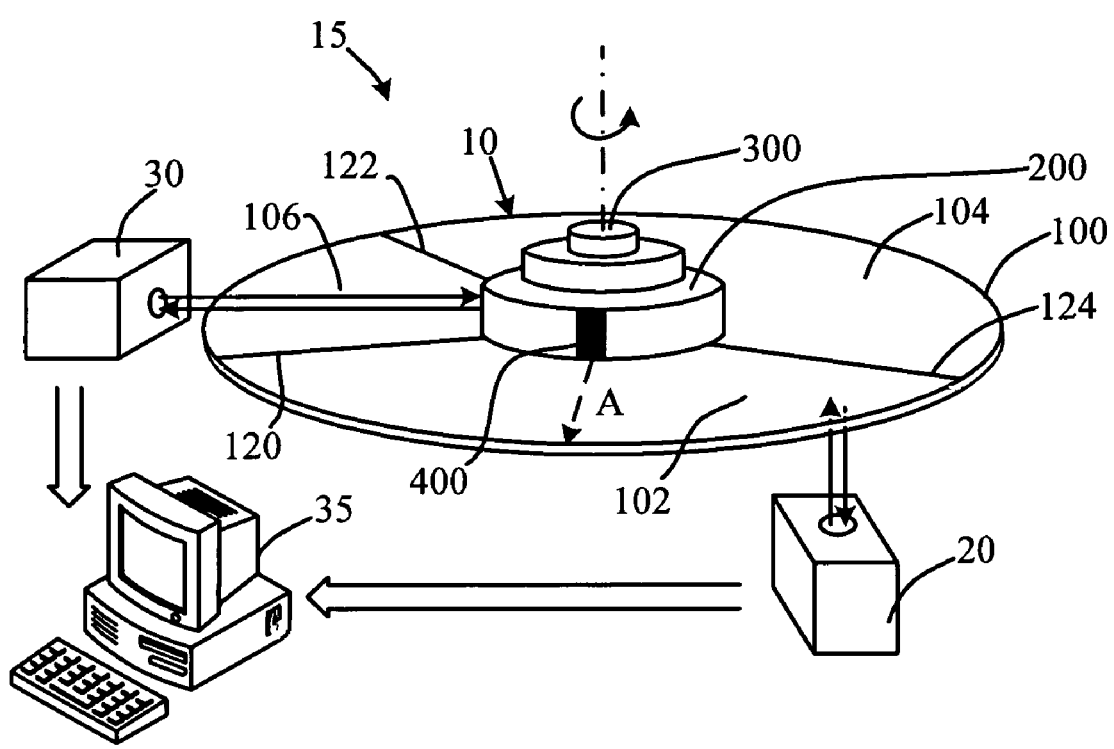
FIG. 1 is a schematic view of a testing system according to a first embodiment of the present invention.

Referring to FIG. 1, the color wheel 10 includes a round color filter 100, a mounting portion 200, a motor 300, and a timing mark 400 on a sidewall of the mounting portion 200. The timing mark 400 has a different reflectivity characteristic than the sidewall, which is accomplished by the timing mark 400 being of a different color, or having a different surface finish, than the sidewall. The color filter 100 comprises three sector-shaped filter segments 102, 104, 106 (which may be red, green, and blue respectively). The filter segments 102, 104, 106 of the color filter 100 may have different central angles from each other. Three boundaries 120, 122, 124 are formed between adjacent filter segments 102 and 106, 106 and 104, and 104 and 102 of the color wheel 10, respectively.

A testing system 15 includes a first sensor 20, a second sensor 30, and a processor 35. The first and second sensors 20, 30 emit light toward the color wheel 10 and receive light reflected back by the color wheel 10, thereby generating impulse signals based on changes in intensity of the light received.

The first sensor 20 is located just below the color filter 100. During operation of the testing system 15, the color filter 100 uniformly rotates with the motor 300, and the first sensor 20 emits light toward the color filter 100. Some of the light is reflected back by the filter segments 102, 104, 106 of the color filter 100 and received by the first sensor 20. Since each of the filter segments 102, 104, 106 only allows light of a corresponding color to pass through, the intensities of the light reflected back by the different filter segments 102, 104, 106 of the color filter 100 are different from each other. The intensity of the reflected light, which is received by the first sensor 20, accordingly changes during the rotation of the color wheel 10. The first sensor 20 detects the changes in intensity of the reflected light and accordingly generates a first impulse signal 40.

Figure 2:
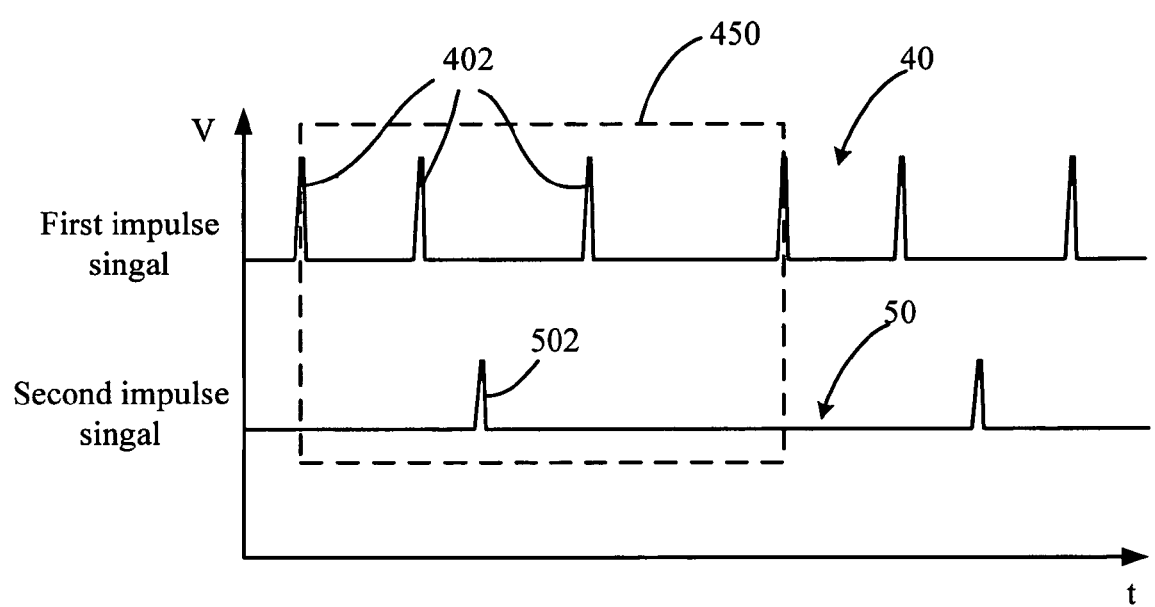
FIG. 2 is a schematic view of waves of impulse signals generated by the testing system of FIG. 1.

Referring to FIG. 2, the first impulse signal 40 includes three peaks, i.e. three boundary impulses 402, in one time period 450. The boundary impulses 402 are generated by the first sensor 20 corresponding to the light reflected at the boundaries 120, 122, 124 between the filter segments 102, 104, 106. The time period 450 is defined by a time interval between two boundary impulses 402 of the first impulse signal 40 corresponding to the same boundary, e.g. the boundary impulse generated corresponding to the boundary 120 between the red and blue filter segments 102 and 106. In this embodiment, the time period 450 is defined by a time interval between four adjacent peaks of the first impulse signal 40. During one time period 450, the color filter 100 rotates approximately 360 degrees, which equates to the sum of the central angles of the red, green and blue filter segments 102, 104, 106. Therefore, a proportion of time intervals defined between each pair of adjacent boundary impulses 402 of one time period 450 equate to a proportion of the central angles of the red, green and blue filter segments 102, 104, 106. Thus, the central angles of the red, green and blue filter segments 102, 104, 106 can be calculated accordingly.

The second sensor 30 faces the sidewall of the mounting portion 200. During rotation of the color wheel 10, the second sensor 30 emits light toward the sidewall of the mounting portion 200 on which the timing mark 400 is located. The light is reflected back from the sidewall of the mounting portion 200 and the timing mark 400, and is then received by the second sensor 30. Since the light reflected by the sidewall of the mounting portion 200 is different from that reflected back by the timing mark 400, accordingly, intensity of the light received by the second sensor 30 changes during the rotation of the color wheel 10. The second sensor 30 detects the changes in intensity of the light reflected and accordingly generates a second impulse signal 50.

Referring to FIG. 2, the second impulse signal 50 includes a peak, i.e. a time impulse 502, in one time period 450. The time impulse 502 is generated by the second sensor 30 corresponding to the light reflected by the timing mark 400. In the time period 450, a proportion of time intervals between the time impulse 502 and each boundary impulse 402 is equal to a proportion of angles formed between the timing mark 400 and each boundary 120, 122, 124 of the color wheel 10. In this embodiment, the angle formed between the timing mark 400 and each boundary 120, 122, 124 of the color wheel 10 is defined between a radius A of the color wheel 10 and the timing mark 400, along with each boundary 120, 122, 124 of the color wheel 10. The angles formed between the timing mark 400 and the boundaries 120, 122, 124 of the color wheel 10, i.e. position angles of the timing mark 400, can thus be calculated. The angular position of the timing mark 400 is therefore obtained.

The processor 35 is used for calculating the central angles of the red, green and blue filter segments 102, 104, 106 and the angular position of the timing mark 400 according to the principles disclosed above.

In the testing system 15, the first and the second sensors 20, 30 emit light toward the color wheel 10, and generate the first and the second impulse signals 40, 50 after the light reflected back by different portions of the color wheel 10 is received by the first and second sensors 20, 30. The central angles of the filter segments 102, 104, 106 of the color filter 100 and the angular position of the timing mark 400 are calculated according to the first and second impulse signals 40, 50. By ensuring that the calculated central angles of the filter segments 102, 104, 106 and the angular position of the timing mark 400 meet certain predetermined criteria, imaging quality of a projector system using the color wheel is assured.

Figure 3:
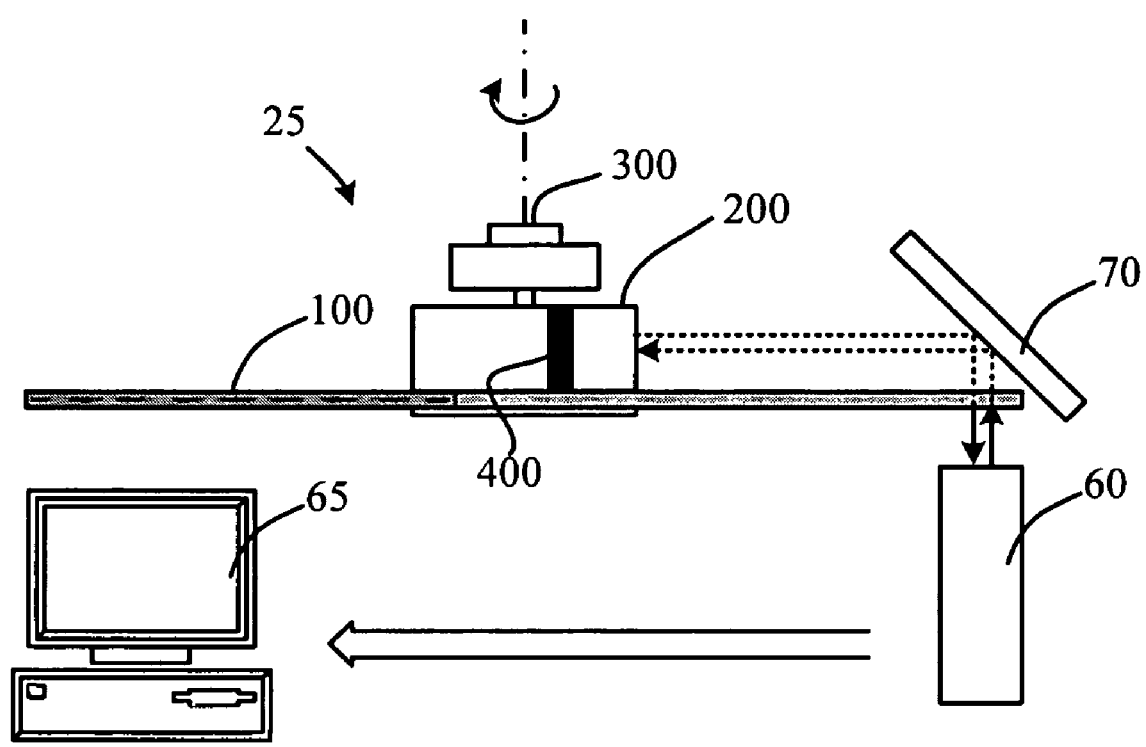
FIG. 3 is a schematic view of a testing system according to a second embodiment of the present invention.

Referring to FIG. 3, a second embodiment of the testing system 25 is shown. The testing system 25 includes a third sensor 60, a reflector 70, and a processor 65. The third sensor 60 is located just below the color filter 100, and emits light toward the filter segments 102, 104, 106 during the rotation of the color wheel 10. Some of the light emitted from the third sensor 60 is reflected back by the filter segments 102, 104, 106, while the remaining light passes through them. The light that has passed through the filter segments 102, 104, 106 is reflected toward the sidewall of the mounting portion 200 by the reflector 70, which faces the sidewall of the mounting portion 200 at a 45-degree angle with respect to the color filter 100 of the color wheel 10. The light reflected toward the sidewall of the mounting portion 200 is reflected back to the reflector 70, which then reflects the light to the color filter 100. Next, the reflected light passes through the filter segments 102, 104, 106 and is received by the third sensor 60. The third sensor 60 then generates a third impulse signal 80 according to the changes in intensity of the reflected light.

Figure 4:
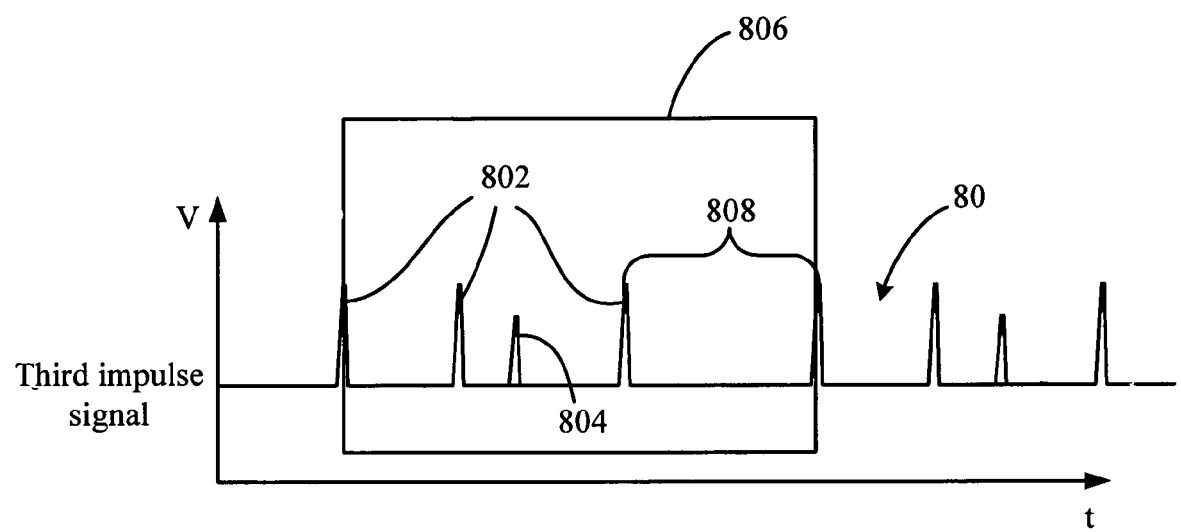
FIG. 4 is a schematic view of an impulse signal generated by the testing system of FIG. 3.

Referring to FIG. 4, the third impulse signal 80 includes four peaks, i.e. three boundary impulses 802 and a time impulse 804 in one time period 806. The time period 806 is defined by a time interval between two peaks of the third impulse signal 80 corresponding to one of the boundaries. A time span 808 is defined as the time interval between adjacent peaks of the time period 806. In FIG. 4, the first and last of five adjacent peaks of the third impulse signal 80 are found to be uniform/equal, and therefore define the time period 806. A proportion of each time span 808 of the time period 806 equates to a proportion of a corresponding angle formed between adjacent boundaries 122 and 120, 124 and 122 or the timing mark 400 and adjacent boundaries 120, 124. The angular position of the timing mark 400 and the central angles can be calculated accurately by the processor 65. For example, if a proportion of the time intervals 808 of the time period 806 is 3:1:3:5, the angle formed between the boundaries 122 and 120 is equal to 90 degrees, the angle formed between the boundary 120 and the timing mark 400 is equal to 30 degrees, the angle formed between the timing mark 400 and the boundary 124 is equal to 90 degrees, and the angle formed between the boundaries 124 and 122 is equal to 150 degrees.

Figure 5:
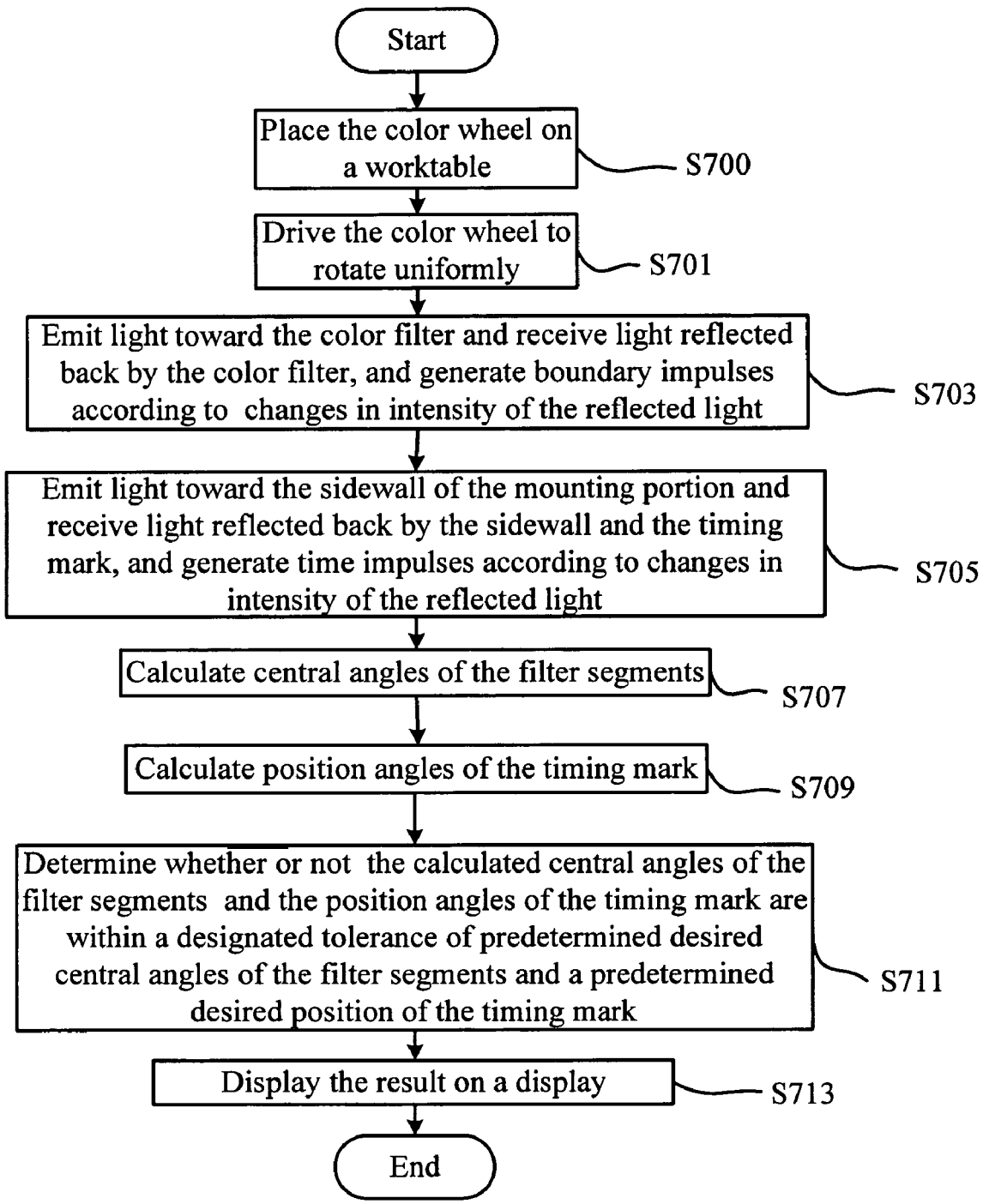
FIG. 5 is a flow chart of a testing method according to the first embodiment of the present invention.

Referring to FIG. 5, a flow chart of the first embodiment of a method for testing a color wheel is shown. The first embodiment of the method corresponds to the testing system 15 shown in FIGS. 1 and 2, and includes the following steps:

Step S700: Place the color wheel 10 on a worktable.

Step S701: Use the motor 300 to drive the color filter 100 and the mounting portion 200 to rotate together uniformly.

Step S703: Emit light toward the color filter 100 of the color wheel 10, receive light reflected back by the color filter 100, and generate a first impulse signal 40 according to changes in intensity of the reflected light. The first impulse signal 40 includes three boundary impulses 402 in one time period 450. The boundary impulses 402 are generated according to the light reflected back by the boundaries 120, 122, 124 of the color filter 100.

Step S705: Emit light toward the sidewall of the mounting portion 200 on which the timing mark 400 is located and receive light reflected back by the sidewall of the mounting portion 200 and the timing mark 400, thereby generating a second impulse signal 50 based on changes in intensity of the reflected light. The second impulse signal 50 includes a time impulse 502 in one time period 450. The time impulse 502 is generated according to the light reflected back by the timing mark 400.

Step S707: Calculate central angles of the filter segments 102, 104, 106 of the color filter 100 according to time intervals between the boundary impulses 402 of the first impulse signal 40.

Step S709: Calculate angles formed between the timing mark 400 and each of the boundaries 120, 122, 124 of the color filter 100, i.e. position angles of the timing mark 400, according to time intervals between the time impulse 502 of the second impulse signal 50 and the boundary impulses 402 of the first impulse signal 40. The angular position of the timing mark 400 on the color wheel 10 is therefore obtained.

Step S711: Determine whether or not the calculated central angles of the filter segments 102, 104, 106 and the position angles of the timing mark 400 are within a designated tolerance of predetermined desired central angles of the filter segments 102, 104, 106 and a predetermined desired position of the timing mark 400, respectively, to decide whether the color wheel 10 satisfies quality requirements.

Step S713: Display the result on a display of the processor 35.

From the steps above, Steps S703 and S705 can be interchanged, i.e. Step S705 can be executed before Step S703, or Steps S703 and S705 can be executed simultaneously.

Figure 6:
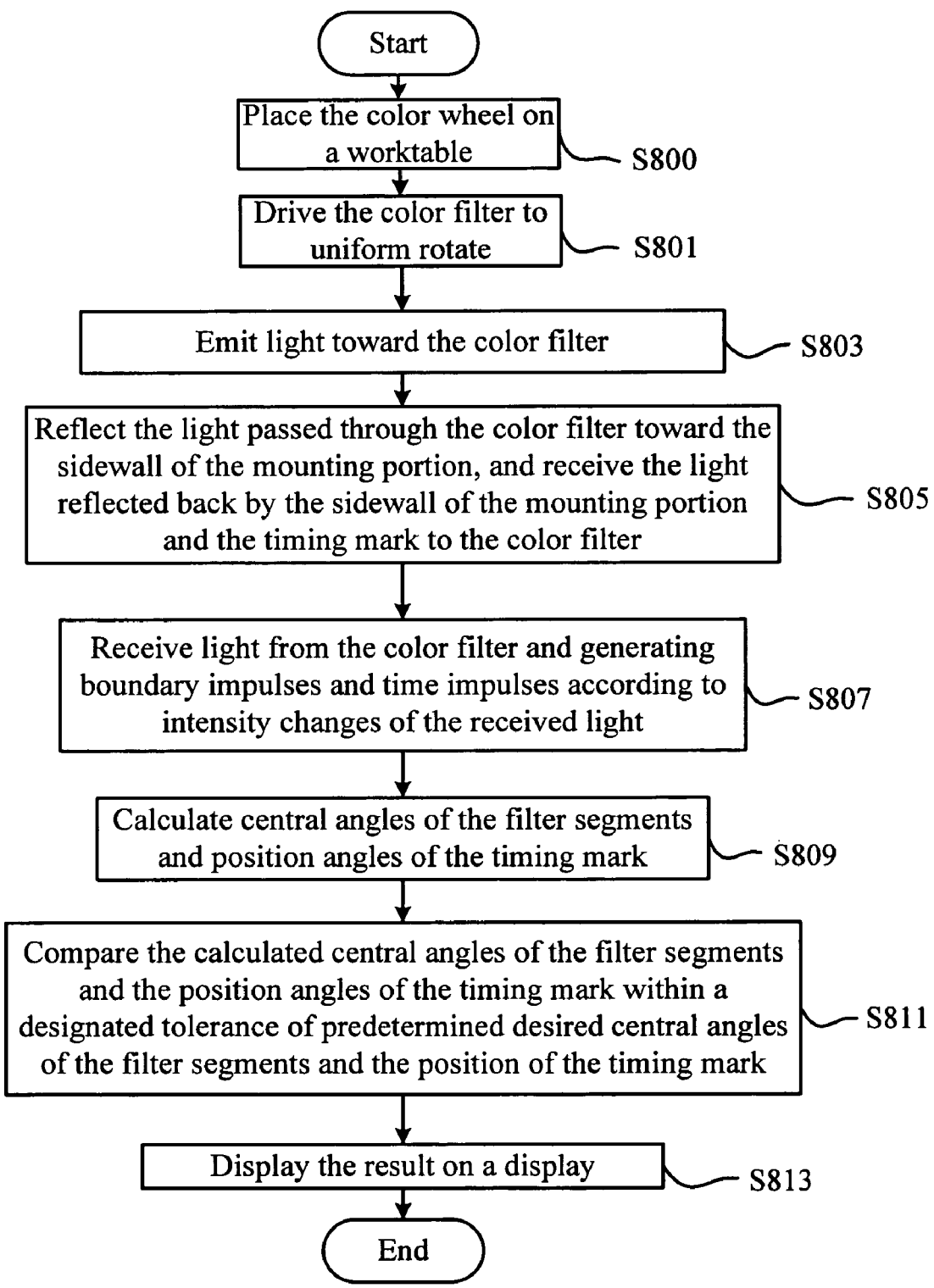
FIG. 6 is a flow chart of a testing method according to the second embodiment of the present invention.
Figure 7:
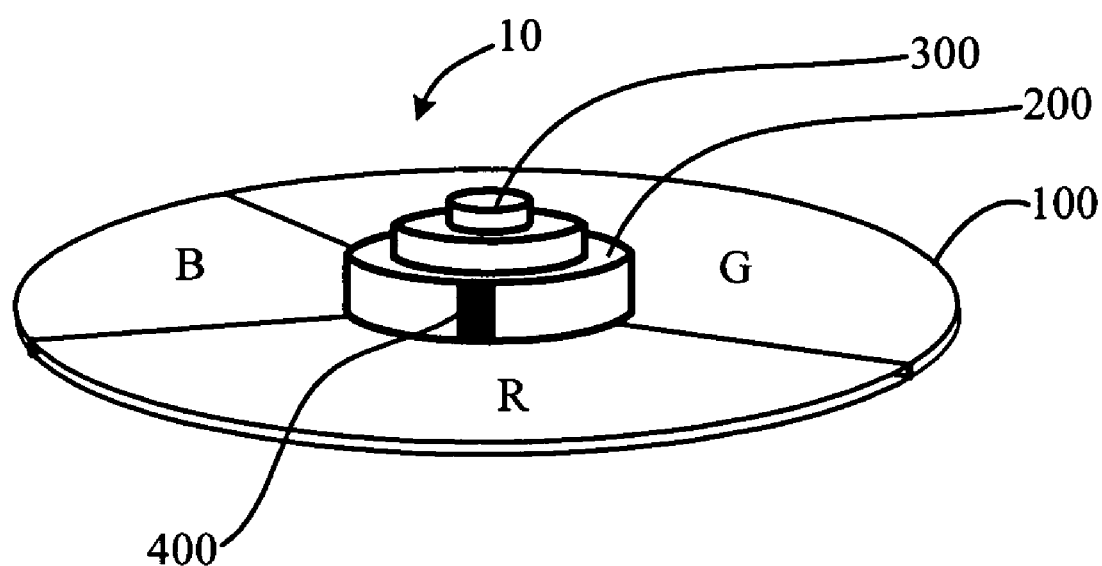
FIG. 7 is a schematic, isometric view of a color wheel of a projector system according to a related art.
Figure 8:
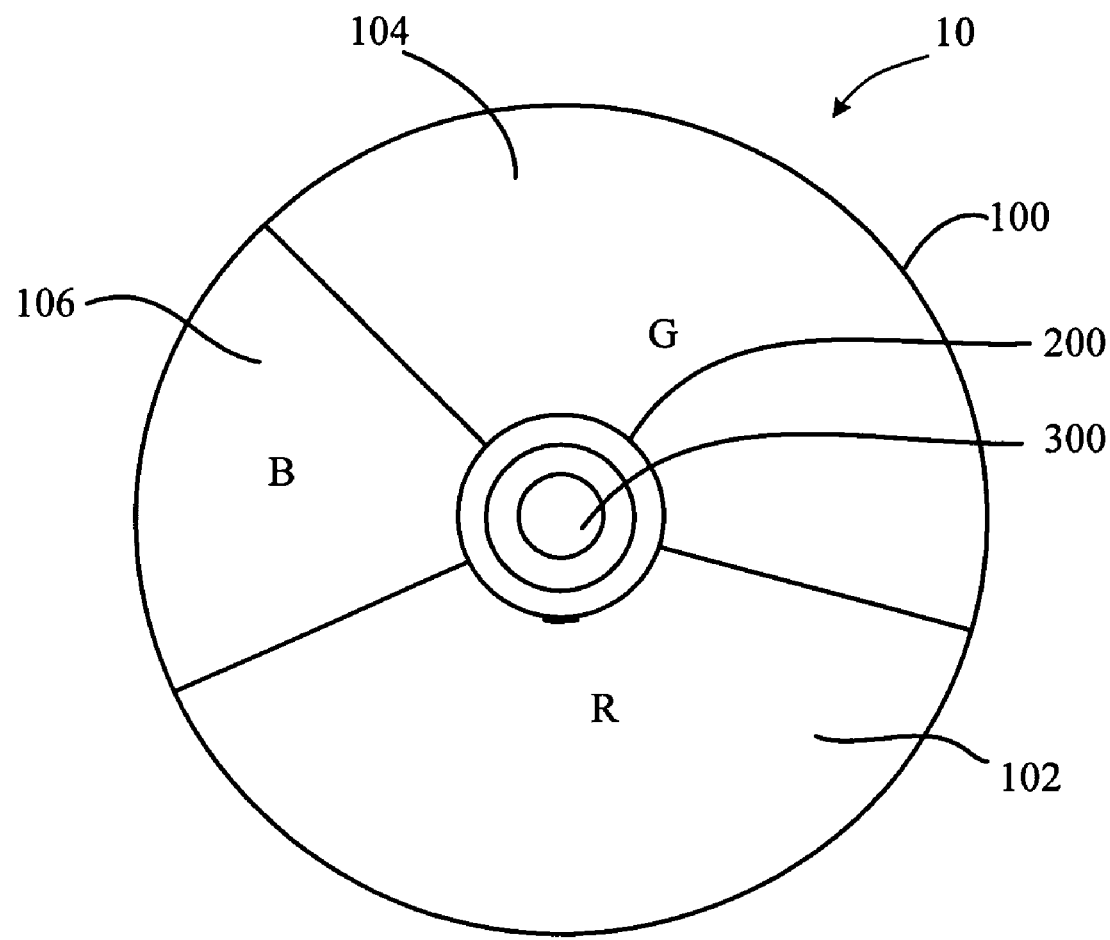
FIG. 8 is a top view of the color wheel of FIG. 7.

Referring to FIG. 6, a flow chart of a second embodiment of the method is shown. The second embodiment of the method corresponds to the testing system 25 shown in FIGS. 3 and 4, and includes the following steps:

Step S800: Place the color wheel 10 on a work table.
Step S801: Drive the color filter 100 to rotate uniformly.
Step S803: Emit light toward the color filter 100 of the color wheel 10.
Step S805: Reflect the light passed through the color wheel 10 toward the sidewall of the mounting portion 200 on which the timing mark 400 is located, and receive the light reflected back by the sidewall of the mounting portion 200 and the timing mark 400 to the color filter 100.
Step S807: Receive the light from the color filter 100 and generate an impulse signal 80 according to changes in intensity of the received light. The light from the color wheel 10 includes two kinds of lights, i.e. the light directly reflected back by the color filter 100, and the light that passes through the color filter 100 after having been reflected by the sidewall of the mounting portion 200 and the timing mark 400. The impulse signal 80 includes a plurality of boundary impulses 802 that are generated according to the light reflected by the boundaries of the color filter 100, along with a plurality of time impulses 804 that are generated according to the light reflected by the timing mark 400.
Step S809: Calculate central angles of the filter segments 102, 104, 106 of the color filter 100 and the angles formed between the timing mark 400 and the filter segments 102, 104, 106 according to relationships between the boundary impulses 802 and the time impulse 804 of the impulse signal 80. The central angles of the filter segments 102, 104, 106 of the color filter 100 are calculated according to time intervals between the boundary impulses 802. The angles formed between the timing mark 400 and the filter segments 102, 104, 106, i.e. position angles of the timing mark 400, are calculated according to time intervals between the time impulse 804 and the boundary impulses 802. The angular position of the timing mark 400 on the color wheel 10 is therefore obtained.
Step S811: Compare the calculated central angles of the filter segments 102, 104, 106 and the position angles of the timing mark 400 with predetermined central angles of the filter segments 102, 104, 106 and a predetermined position of the timing mark 400, respectively, to determine whether the color wheel 10 satisfies the quality requirements.

Step S813: Display the result on a display of the processor 35.

It is to be understood, however, that even though numerous characteristics and advantages of the present invention have been set forth in the foregoing description, along with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A testing method configured for testing parameters of a color wheel, the color wheel comprising a color filter comprising several sector-shaped filter segments and a motor for driving the filter segments of the color filter to rotate, the testing method comprising:
rotating the color filter;
emitting light toward the color filter of the color wheel and receiving light reflected back by the color filter, and generating a plurality of boundary impulses based on changes in intensity of the light reflected; and
calculating central angles of the filter segments of the color filter based on relationships between the boundary impulses.

2. The testing method of claim 1, wherein the central angles of the filter segments of the color filter are calculated according to time intervals between the boundary impulses.

3. The testing method of claim 1, wherein the color wheel further comprises a timing mark located on a sidewall of a mounting portion of the color wheel, the timing mark and the sidewall co-rotated with the filter segments, the testing method further comprising:
emitting light toward the sidewall of the mounting portion and the timing mark, receiving light reflected back by the timing mark and the sidewall, and generating a time impulse due to changes in intensity of the light reflected; and
calculating a position angle of the timing mark on the color wheel due to relationships between the boundary impulses and the time impulse.

4. The testing method of claim 3, wherein the position angle of the timing mark on the color wheel is calculated according to time intervals between the boundary impulses and the time impulse.

5. The testing method of claim 3, further comprising:
determining whether or not the calculated central angles of the filter segments and the position angle of the timing mark are within a designated tolerance of predetermined desired central angles of the filter segments and a predetermined desired position of the timing mark, respectively, to decide whether the color wheel satisfies quality requirements; and
displaying the result on a display.

6. The testing method of claim 3, wherein the light emitted toward the filter segments is emitted by a first sensor located just below the color filter, and the light emitted toward the sidewall of the mounting portion and the timing mark is emitted by a second sensor facing the sidewall of the mounting portion.

7. The testing method of claim 1, wherein the color wheel further comprises a timing mark located on a sidewall of the color wheel, and the timing mark and the sidewall co-rotate with the filter segments, the testing method further comprising:

receiving light passing through the color filter and reflected back by the timing mark and the sidewall, and generating a time impulse due to changes in intensity of the light reflected; and calculating a position angle of the timing mark on the color wheel according to relationships between the boundary impulses and the time impulse.

8. The testing method of claim 7, further comprising:

determining whether or not the calculated central angles of the filter segments and the position angle of the timing mark are within a designated tolerance of predetermined desired central angles of the filter segments and a predetermined desired position of the timing mark, respectively, to decide whether the color wheel satisfies quality requirements; and displaying the result on a display.

9. The testing method of claim 7, wherein the position angle of the timing mark on the color wheel is calculated according to time intervals between the boundary impulses and the time impulse.

10. The testing method of claim 7, wherein the light is emitted and received by a sensor located just below the color filter.

11. The testing method of claim 7, wherein the light passing through the color filter is reflected toward the sidewall and the timing mark by a reflector which further reflects light from the sidewall of the mounting portion and the timing mark toward the color filter.

12. The testing method of claim 11, wherein the reflector forms a 45-degree angle with respect to the color filter.

13. The testing method of claim 7, wherein the color filter rotates with the motor at a uniform speed.

* * * * *